(12) United States Patent
Wang et al.

(10) Patent No.: US 7,336,861 B2
(45) Date of Patent: Feb. 26, 2008

(54) FIBER-OPTIC SENSOR OR MODULATOR USING TUNING OF LONG PERIOD GRATINGS WITH SELF-ASSEMBLED LAYERS

(75) Inventors: Zhiyong Wang, Clifton Park, NY (US); James R. Heflin, Jr., Blacksburg, VA (US); Siddharth Ramachandran, Hoboken, NJ (US)

(73) Assignees: Virginia Tech Intellectual Properties, Inc., Blacksburg, VA (US); Furukawa Electric North America, Norcross, GA (US)

( * ) Notice: Subject to any disclaimer, the term of this patent is extended or adjusted under 35 U.S.C. 154(b) by 0 days.

(21) Appl. No.: 11/397,054

(22) Filed: Apr. 4, 2006

(65) Prior Publication Data

US 2007/0025661 A1 Feb. 1, 2007

Related U.S. Application Data

(60) Provisional application No. 60/667,673, filed on Apr. 4, 2005.

(51) Int. Cl.
*G02B 6/00* (2006.01)

(52) U.S. Cl. .............................. 385/12; 385/15; 385/31; 385/37

(58) Field of Classification Search .................. 385/12, 385/15, 31, 37
See application file for complete search history.

(56) References Cited

U.S. PATENT DOCUMENTS

| | | |
|---|---|---|
| 6,950,578 B1 | 9/2005 | Ramachandran |
| 2005/0002606 A1 * | 1/2005 | James et al. .................. 385/31 |
| 2005/0025422 A1 * | 2/2005 | Magnusson et al. .......... 385/37 |

* cited by examiner

*Primary Examiner*—Jennifer Doan
(74) *Attorney, Agent, or Firm*—Whitham, Curtis, Christofferson & Cook, PC

(57) ABSTRACT

The provision of an ionic self-assembled multilayer (ISAM) film on a fiber-optic element including a long period grating (LPG) by a simple, room temperature process provides tuning of the LPG and/or high sensitivity to the refractive index of the ambient environment of the fiber-optic element. Inclusion of a final layer or a probe, receptor or affinity ligand in the multi-layer film provides a highly sensitive sensor for specific chemical and biological materials. Use of a turn around point (TAP) LPG allows detection to be performed by detection of light intensity rather than wavelength of attenuation. Use of a material having an electro-optical response to an electrical field by change of dimension or refractive index allows the combination of a LPG or TAP LPG and ISAM film to function as a light modulator.

17 Claims, 11 Drawing Sheets

| Polycation | Polycation pH | Absorbance/Bilayer | Bilayer Thickness, nm | Absorbance/nm |
|---|---|---|---|---|
| PAH | 7 | 0.005 ± 0.001 | 0.3 ± 0.1 | 0.017 |
| PAH | 10 | 0.023 ± 0.003 | 9.2 ± 0.5 | 0.003 |
| PAH | 11 | 0.050 ± 0.014 | 14.1 ± 1.4 | 0.004 |
| PDDA | 7 | 0.003 ± 0.0002 | 0.16 ± 0.0 | 0.02 |
| PDDA | 10 | 0.004 ± 0.0003 | 0.19 ± 0.0 | 0.02 |
| PDDA | 11 | 0.009 ± 0.002 | 11.2 ± 0.9 | 0.001 |

Figure 3D

FIBER-OPTIC SENSOR OR MODULATOR USING TUNING OF LONG PERIOD GRATINGS WITH SELF-ASSEMBLED LAYERS

CROSS-REFERENCE TO RELATED APPLICATIONS

This application claims priority of U.S. Provisional Patent Application 60/667,673, filed Apr. 4, 2005, which is hereby fully incorporated by reference.

BACKGROUND OF THE INVENTION

1. Field of the Invention

The present invention generally relates to fiber optic sensors and light modulators and, more particularly, to such devices using long period gratings (LPGs) and tuning thereof for sensing or modulation using ionic self-assembled multilayer (ISAM) coatings.

2. Description of the Prior Art

Optical fiber long period gratings (LPGs) are being heavily investigated as key components of a "next-generation" of optical fiber communication systems. Long period gratings are structures formed within an optical fiber, generally by irradiation of the fiber with ultraviolet light using a mask, which produce diffraction of light such that certain wavelengths are strongly attenuated with extremely high selectivity while other wavelengths are substantially less affected. More specifically, long period fiber gratings (LPGs) couple light between copropagating modes of an optical fiber and, due to their compactness, low insertion loss and low back reflection, have been used as spectral shapers and mode converters in optical fiber communication systems. In addition, LPGs that couple the fundamental mode of a single mode fiber (SMF) to one of its cladding modes are ultra-sensitive to the refractive index of the material surrounding the fiber. This high sensitivity and high resolution have led to extensive investigations of LPGs for use as chemical and biological sensors and other index modulating fiber devices. However, reproducible fabrication of such LPGs is non-trivial; often yielding LPGs which attenuate somewhat different wavelengths without perfect predictability of the wavelength which will be most strongly attenuated or the amount of attenuation of a given wavelength. Therefore, there has been great interest in developing techniques by which LPGs can be fine-tuned in a simple manner after basic manufacture.

There is a rapidly growing demand for chemical sensors and bio-sensors having high sensitivity and ease of use. Uses range from environmental monitoring to medical diagnostics to detection of chemical and bio-chemical warfare agents. Thus, the variety of chemical agents to be detected is similarly wide-ranging: including but not limited to DNA hybridization microarrays, drug/protein interactions, protein/protein interaction and the like, possibly extendable to the sensing of the presence of non-biological agents. However, many known sensors, not necessarily using LPGs, rely on adsorption of or interaction with a particular material and may be of greater or lesser specificity than may be desired and/or may require labeling of materials to be detected with another material and, in any case, may not be capable of re-use after a single episode of detection is performed due to irreversible interactions or the presence of captured materials which are not easily removable.

Optical modulation is the key to fiber-optical communication systems. A further important factor is the insertion loss of the modulator mechanism across optical boundaries from and to optical fiber links. For this latter reason, in particular, LPGs have caused substantial interest since their optical activity is achieved "in-line" within a length of optical fiber such that boundaries at which light loss may occur may, in principle, be eliminated. However, modulation in an LPG requires reversible tuning at extremely high frequencies; foreseeably at and above 150 GHz.

Normally, the index sensitivity of LPGs is attributed to the index of the bulk medium surrounding the fiber, and features with sub-wavelength sizes are not expected to modulate the resonance of LPGs. However, it has been demonstrated that switching and sensing devices could be achieved by using adsorption or desorption of a monolayer of water molecules on the surface of a short period relief grating coupler fabricated on planar waveguides. More recently, it has been reported that resonant shifts in LPGs have been observed with films of sub-wavelength thickness, using Langmuir-Blodgett (LB) films. The observed optical response was relatively small with maximal shifts of 10 nm in wavelength with 400 nm of deposited film. Moreover, LB films are not amenable to practical device construction. This is because the LB technique has demanding requirements of expensive special equipment to precisely control the pressure on the liquid surface and is relatively slow. More significantly, films deposited by the LB technique show poor mechanical and thermal stability because the van Der Waals interaction is the primary binding mechanism.

Ionic self-assembled multilayers (ISAM), on the other hand, are formed by a layer-by-layer deposition technique and exhibit enhanced reliability, stability and film quality in comparison to LB films. Through alternately immersing a charged substrate into anionic and cationic polyelectrolyte aqueous solutions, a nano-scale multi-layer thin film is built by consecutive adsorption of polyanions and polycations onto a solid substrate driven by electrostatic forces. The ISAM fabrication method provides a highly controllable means to build precise, nm-thick films on surfaces (indeed, they can be incorporated on any surface with a minimum charge density, such as metals, glass, or silica). Thus, compared with the LB technique, ISAM technique shows more flexibility on choices of substrate or template and thin-film overlay materials for devices.

Extensive bibliographic information concerning research relevant to the background of the present invention as discussed above is provided in the above-incorporated U.S. Provisional Patent Application. Nevertheless, it has not been shown that films can be developed by the ISAM process which allow LPGs to be used for practical chemical and/or biological agent detection, much less to form a sensor which is reusable or a practical optical modulator in the frequency ranges needed for practical fiber-optic communication systems capable of currently required performance.

SUMMARY OF THE INVENTION

It is therefore an object of the present invention to provide a simple and economical fiber optic structure for providing reliable, repeatable and highly selective tuning of a long period fiber-optic grating.

It is another object of the present invention to provide a reusable chemical and biological agent sensor of high sensitivity and resolution.

It is further object of the invention to provide an economical in-line fiber-optic modulator capable of light modulation in the frequency range of 150 Ghz and above.

In order to accomplish these and other objects of the invention, an optical device is provided comprising, in combination, a fiber-optic element including a long period grating therein, a multi-layer film having a higher index of refraction than said optical fiber element, and an ambient environment.

In accordance with another aspect of the invention, a chemical sensing or biosensor apparatus is provided comprising a fiber-optic element including a long period grating therein, a multi-layer film having a higher index of refraction than said optical fiber element and a layer of probe or receptor molecules, and an arrangement for detecting changes of light attenuation in said fiber-optic element.

In accordance with a further aspect of the invention, a fiber optic communication system is provided comprising a fiber-optic element including a long period grating therein, a multi-layer film adjacent said fiber-optic element having a higher index of refraction than said optical fiber element, said multi-layer film including a layer of material exhibiting and electro-optical response to an electric field, and an electrode for applying an electrical field to said multi-layer film.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1A:
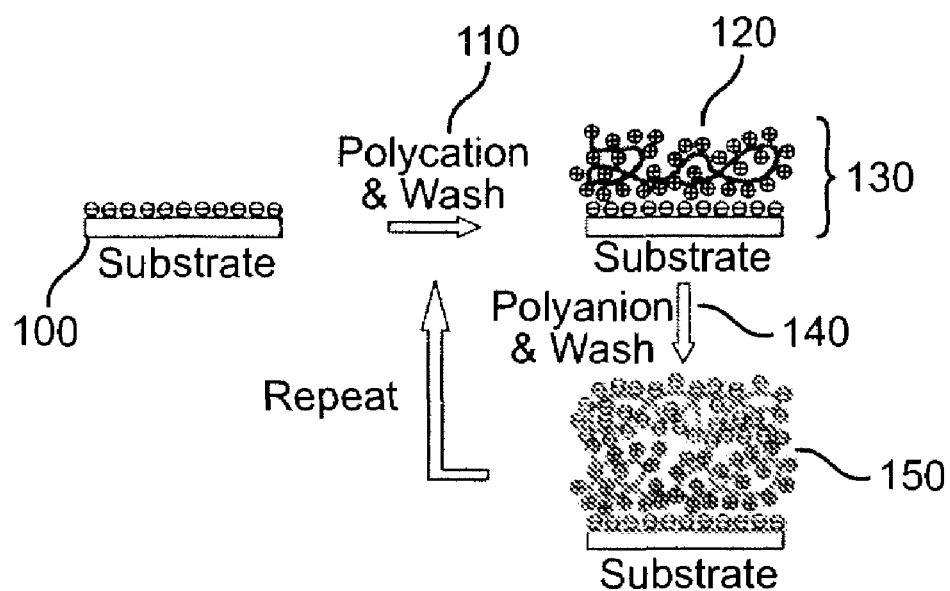
FIGS. 1a and 1b illustrate a method of developing an ISAM film on a fiber optic LPG and a cross-sectional view of a surface thereof, respectively, FIG. 2 graphically illustrates values of total thickness and refractive index of ISAM films as a function of pH of the polyanion and polycation solutions used to form the ISAM film, FIG. 3a graphically illustrates experimental results of LPGs with ISAM films as a function of number of ISAM bilayers or thickness, FIG. 3b graphically illustrates the change in resonant wavelength as a function of the film thickness for a variety of pH combinations of PAH and PCBS solutions forming bilayers of the ISAM film.

Referring now to the drawings, and more particularly to FIG. 1a, the preferred and generalized method of applying an ionic self-assembled multi-layer (ISAM) film (also referred to as a layer-by-layer (LBL) film) to a fiber optic LPG is illustrated. It should be understood that this generalized method provides a basic technique for providing tuning of fiber optic LPGs. Variations thereof and additional perfecting features supporting the function of such a structure as a chemical sensor or bio-sensor and as a modulator for fiber optic communication systems will be discussed below. However, the discussion of FIGS. 1a and 1b and the experimental results illustrated in FIG. 2 and FIGS. 3a and 3b will provide an understanding of the basic structure of and employed by the invention and its basic principles sufficient to enable its successful construction and use.

The inventors are the first to have achieved deposition of ISAM films of nm-thicknesses that are deposited on LPGs and to have observed the resonance tuning of fiber-optic LPGs having such a structure. Record shifts in the resonant wavelength (40 nm) were observed for film thicknesses of only 25 nm. Fine control of the refractive index and the thickness of the ISAM film was achieved by altering the relative fraction of the anionic and cationic materials combined with layer-by-layer deposition. Further the inventors have demonstrated the feasibility of this highly controllable deposition technique for fine-tuning grating properties. These demonstrations, combined with the fact that ISAMs can incorporate a variety of chemical and biological sensing elements, provides for a robust platform for building sensors.

The ISAM deposition process involves the immersion of a charged substrate into aqueous solutions of polyanions and polycations (at room temperature) in alternating sequence. High vacuum, high temperature, organic solvents or clean room facilities are not required. The nano-scale multilayer thin film is built by consecutive adsorption of polyanions and polycations onto a solid substrate driven by electrostatic forces. The resulting macroscopic properties of the thin film are determined by the properties of individual molecules as well as the dipping solution properties (e.g. pH, ionic strength, and concentration) and the dipping sequence of the thin film.

The process is schematically shown in FIG. 1a. First, the substrate 100 is washed (110), preferably using deionized water, and the clean, substrate is negatively charged and dipped into the polycation solution. Due to the strong coulombic attraction between the negatively charged substrate and the positively charged polycation, a layer of polycation molecules 120 is deposited on the substrate as shown at 130. The film growth requires that the materials for each successive layer possess multiple charges so that the surface charge on the substrate can be reversed(e.g. from positive to negative) as each layer is adsorbed. A reversal to positive surface charge results, which limits further polycation adsorption. Then the polycation-coated substrate is removed from the solution and rinsed with deionized water (140) to remove excess polycation molecules that are not ionically bound. The substrate is then immersed into the polyanion solution to adsorb a layer of polyanion molecules 150 onto the substrate 100 driven by the coulombic attraction to the positive surface charge developed by the deposited polyanion molecules. Each layer may be controllably varied in thickness from about 0.3 nm or less to about 20 nm, dependent on materials and preparation conditions, and are exceptionally uniform at the molecular level as shown by studies using optical absorption, ellipsometry and X-ray diffraction. Finally, these steps are repeated to obtain a multilayered thin-film with an (AB)n architecture until the desired film thickness is reached. The combination of one layer of polycation and polyanion together is denoted a bilayer and the process may be initiated as discussed above or using a positive charge and a polycation solution to form the initial layer.

The growth of multi-layer films using this technique was first demonstrated using synthetic polyelectrolytes, but has now been demonstrated to be applicable to proteins, fullerenes, metal colloids, clays, and multivalent dye molecules, among other materials. The potential applications of the ISAM technique have only begun to be explored, but already include polymeric light-emitting diodes, photovoltaics, permselective gas membranes, anti-reflection coatings, and electrochromic films. It has also been demonstrated that ISAM films can be fabricated into noncentrosymmetric structures for second order nonlinear optical (NLO) applications.

For the fabrication of ISAM-functionalized LPG's with optimum sensitivity for biosensors, several requirements must be met:

1. control of ISAM thickness and refractive index on the LPG is needed to tune the LPG to maximum sensitivity.
2. control of ISAM surface chemistry is needed to permit the deposition and attachment of affinity ligands that selectively bind to target molecules, thus changing the effective refractive index of the ISAM coating for the sensing step.
3. design and fabrication of novel fibers with unique dispersive properties for the core and cladding modes that yields maximum sensitivity for the range of effective refractive indices achievable by ISAMs.

The refractive index and thickness of the cladding layer on the LPG are among the most critical parameters for sensitivity. The effective refractive index of a thin ISAM film depends on both its actual refractive index and thickness since the optical field senses both the film and the surrounding air or liquid. Importantly, ISAM fabrication allows fine-tuning of the refractive index n by changing the relative fraction of the anionic and cationic materials. This, combined with layer by layer control of film thickness, provides a precise, continuous method for tuning the effective refractive index of the ISAM film adsorbed on an LPG.

Figure 1B:
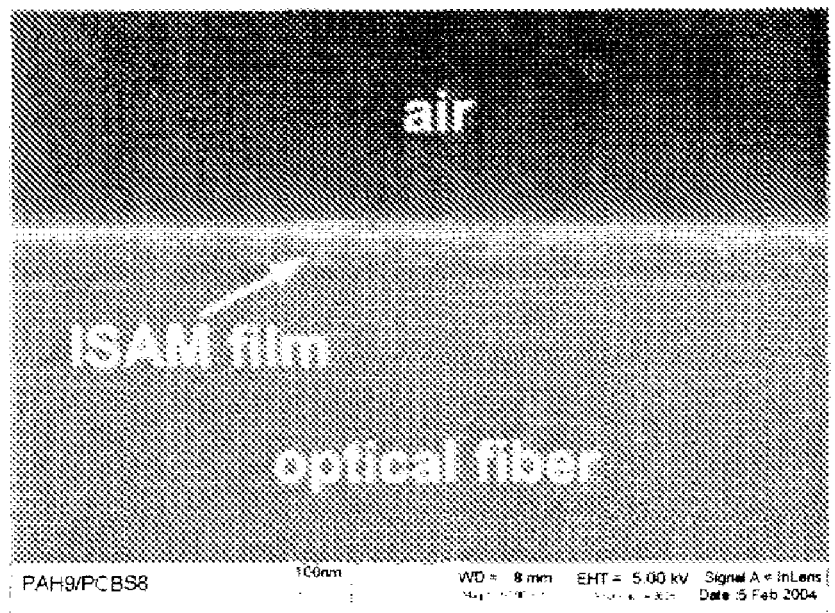
Figure 2A:
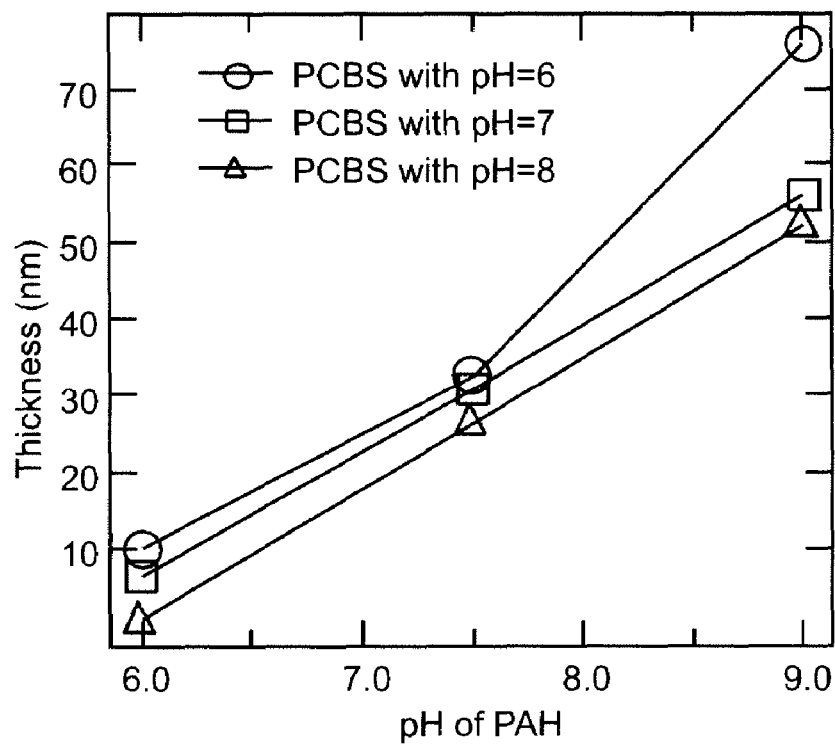
Figure 2B:
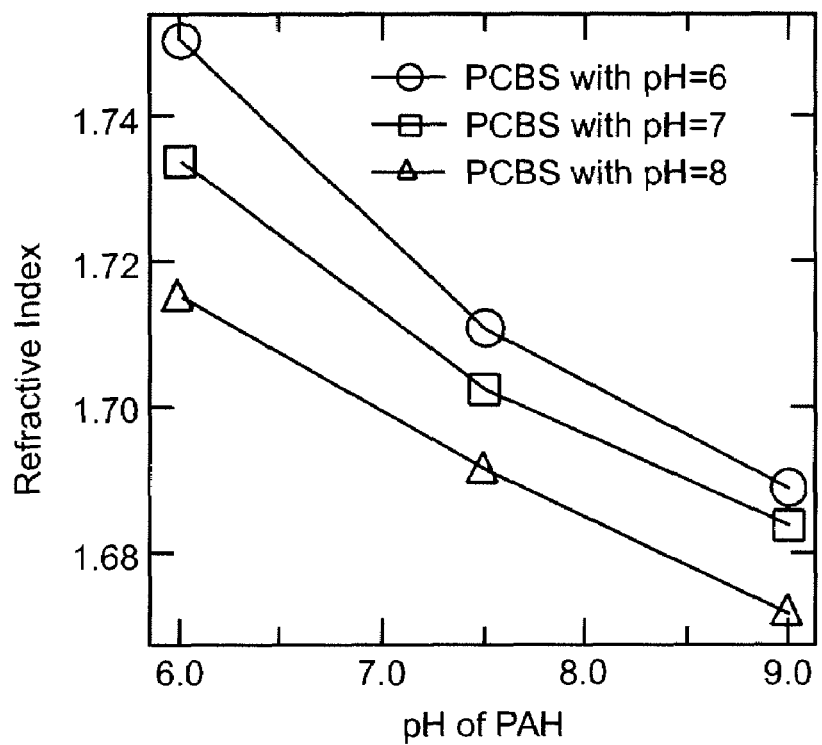

FIG. 1b is a scanning-electron micrograph of the surface of a fiber coated with an ISAM film, showing characteristic thicknesses achieved by this technique.

An investigation of the dependence of the properties of ISAM films on the variation of the pH of the polyanion and polycation solutions by using variable angle spectral ellipsometry was conducted. Standard microscope glass slides were used as substrates. Poly (allylamine hydrochloride) (PAH) at 10 mM concentration was used as polycation, and poly[1-[4-(3-carboxy-4-hydroxy-phenylazo) benzenesulfonamido]-1,2-ethanediyl, sodium salt (PCBS) at 10 mM concentration was used as polyanion. The slides were prepared by the RCA cleaning process. Several samples were fabricated with PAH and PCBS solutions of different pH levels. The pH of the PAH solutions ranged from 6 to 9 and that of the PCBS solutions ranged from 6 to 8, respectively. All samples were prepared by depositing 20 bilayers of PAH/PCBS on the slides.

FIG. 2 shows the values of total thickness $d_{tot}$ and refractive index n as a function of pH of the polyanion/cation solutions. When the pH of the PCBS solution is fixed, $d_{tot}$ increases while n decreases as the pH of the PAH solution increases. In contrast, when the pH of the PAH solution is fixed, both $d_{tot}$ and n decrease as the pH of the PCBS solution increases. The reason for this is that both PAH and PCBS are weak electrolytes such that variations of pH will change the charge density of the adsorbing polymer. Not wishing to be held to any particular theory of this behavior, this behavior is understood as follows—both solutions are fully charged at neutral pH. As the pH is lowered from neutral, the charge density of PCBS decreases since its acid groups become protonated. While, as the pH of the PAH solution is increased, its ammonium groups become deprotonated, and the charge density of PAH will decrease. As charge density decreases, less repulsion between neighboring charges allows more polymer chains to be adsorbed on the substrate with loops and tails to induce thicker layers. Furthermore, since PCBS has a higher refractive index than PAH, a higher percentage of PCBS results in a higher composite index of the ISAM film while a higher percentage of PAH results in lower composite index. Therefore, the thickness and refractive index of ISAM films can be fine-tuned by adjusting the pH values of the polyelectrolyte solutions.

It should be noted that the thickness of the films described in the previous section is of the order of several nm, and their "bulk" refractive indices are significantly higher than that of silica. Normally, this regime would not be very interesting for LPG tuning applications, since LPGs are most responsive to ambient index changes for bulk refractive index values slightly lower than silica. To test the influence of ISAM films on LPGs, different pH values for the PAH and PCBS solutions were utilized in fabricating films. As noted earlier, this film deposition process is agnostic or indifferent to substrate topology or geometry, and thus obtaining cylindrically symmetric ISAM films on fibers requires no additional set up. (In FIG. 1, deposition is depicted only on one surface of the substrate and cladding is omitted for clarity and as more accurately depicting the experimental conditions for initially forming ISAM films in accordance with the invention.) The pH of the PAH solutions for this experiment varied from 7.5 to 9, while the pH of PCBS solutions ranged between 6 and 8. The LPGs were UV-induced on TrueWave™ RS fibers with a grating period of 116 μm and a length of 5 cm. This yielded gratings that couple the fundamental mode to the $LP_{0,12}$ cladding mode at a resonant wavelength of 1420 nm. The transmission spectra were measured by an optical spectrum analyzer after deposition of every five PAH/PCBS bilayers.

Figure 3A:
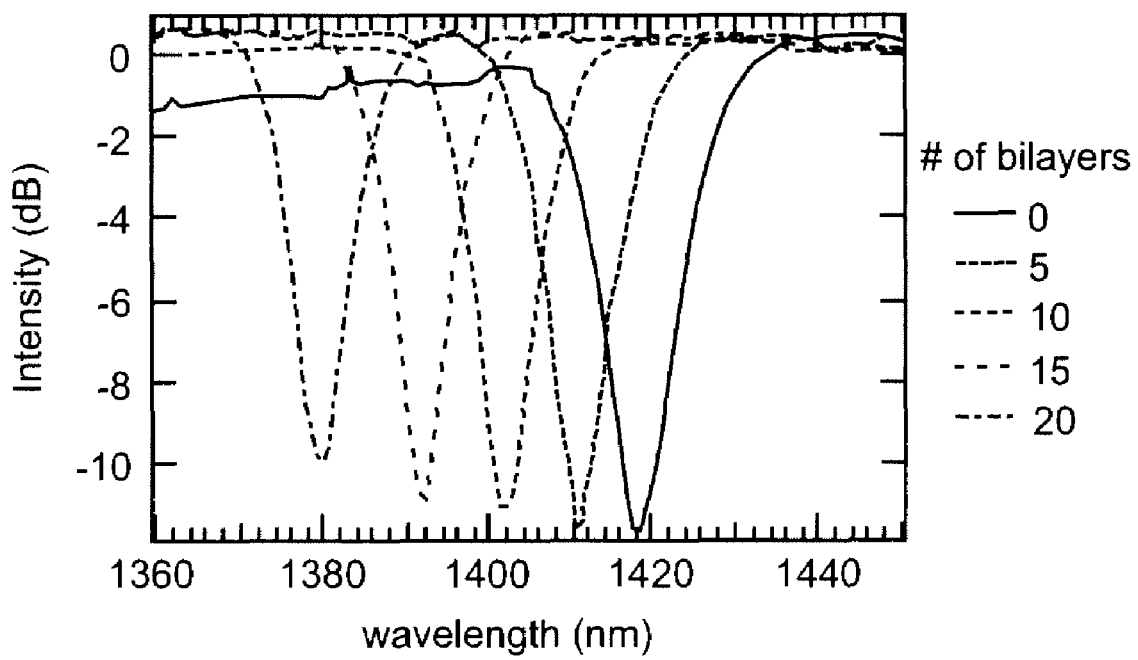
FIG. 3c illustrates chemical structures of polyelectrolytes usable in ISAM films including chromophore-containing PCBS (a), polycation PAH (b), and polycation PDDA (c)
FIG. 3d is a table showing the control of bilayer thickness and film composition For ISAM films made with exemplary polyanions and cations, FIG. 3e graphically illustrate light absorbance at a wavelength of 359 nm as a function of the number of bilayers in an ISAM film using the materials represented in FIG. 3d.
Figure 3B:
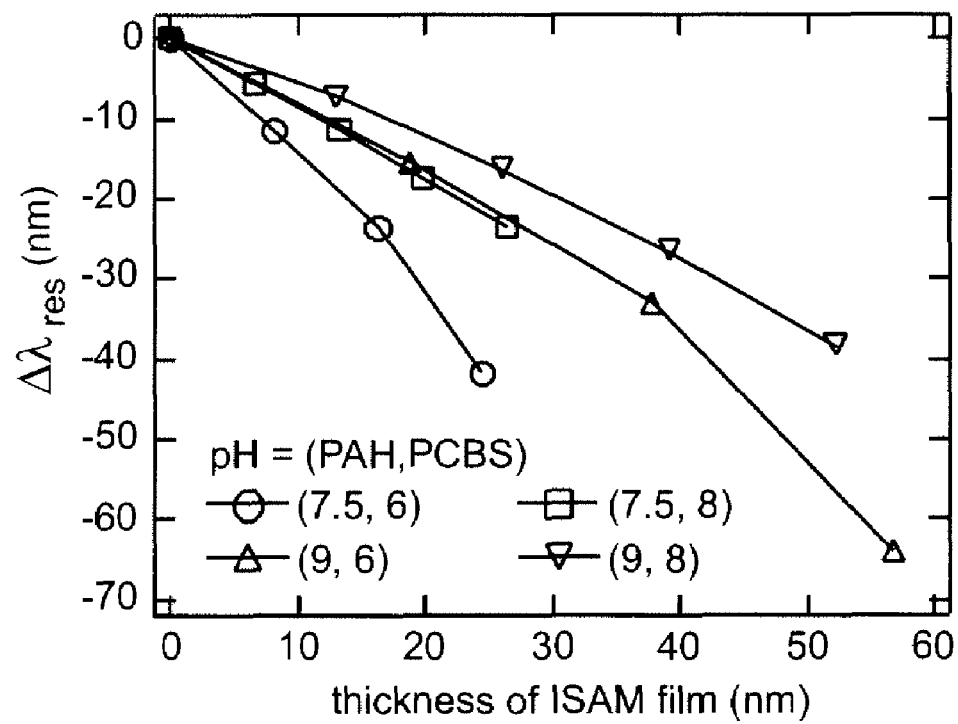

Experimental results of the ISAM-coated LPG are shown in FIGS. 3a and 3b. FIG. 3a shows an example of the shift in the LPG resonance as the number of bilayers of the ISAM film (and hence its thickness) is increased. Note that the shift in the resonance is reminiscent of shifts attributed to increasingly higher ambient index values for an LPG in silica fiber, with the ambient index value remaining lower than that of silica. This is further illustrated in FIG. 3b, which shows the change in resonant wavelength as a function of the film thickness for a variety of pH combinations of PAH and PCBS solutions. A record steep resonant wavelength shift of 1.6 nm/nm is obtained for the case where the pH of PAH is 7.5 and that of PCBS is 6.

A hallmark of ISAM films is the precise control of film composition [25] and bilayer thickness [26] that can be achieved by controlling solution deposition conditions such as pH. To demonstrate that ISAM films can be fabricated with controlled thickness and refractive index, we deposited films on glass microscope slide substrates using the anionic, polymeric dye poly{1-[4-(3-carboxy-4-hydroxyphenylazo)-benzensulfonamido]-1,2-ethanediyl, sodium salt} (PCBS) (FIG. 3c (a). Poly(allylamine hydrochloride) [PAH] and poly(diallyldimethylammonium chloride) [PDDA], (FIG. 3c (b) and (c)) were used as the polycations. Due to its conjugated chromophore side-group, PCBS has a relatively high refractive index n compared to the polycations. Thus the optical properties of ISAM films formed with these polymers can be tuned by varying the composition of these films which, in turn, is controlled by the deposition conditions. The formation of each monolayer is exceptionally rapid with these polymers. Through measurements of absorbance and of film thickness (by ellipsometry) as a function of immersion time, each monolayer was found to be fully deposited in less than one minute of immersion in the polyelectrolyte. This allows the rapid buildup of self-assembled, multilayer films.

Figure 3C:
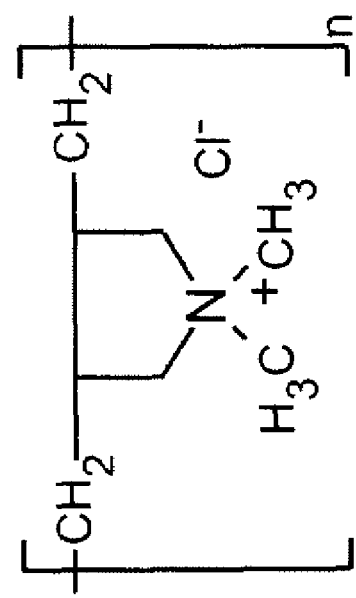
Figure 3C:
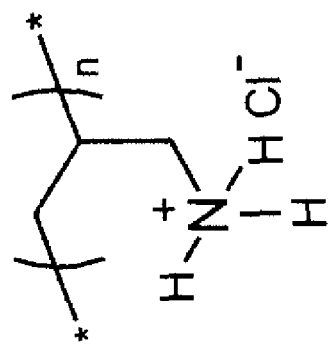
Figure 3C:
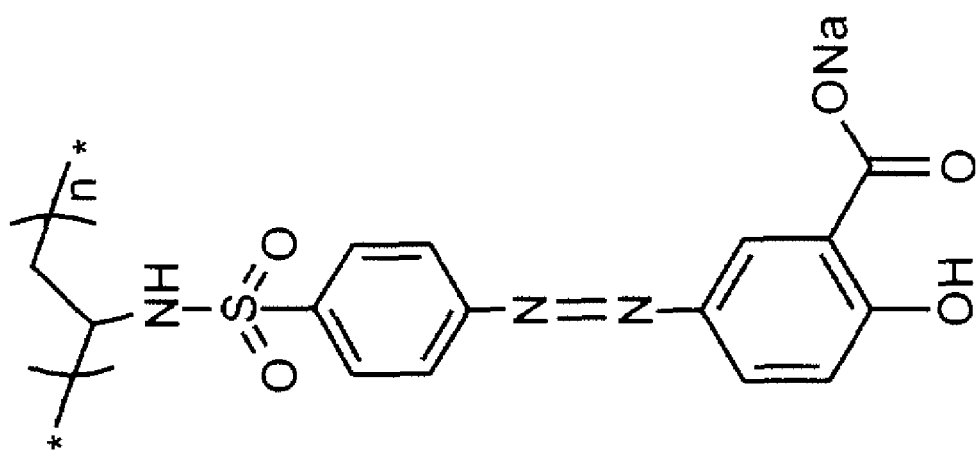

The inventors have also shown that the ISAM film bilayer thickness and composition can be controlled by variation of the pH and ionic strength of the immersion solutions. For example, for PAH, a weak polycation, increased pH reduces the charge density and lowers the solubility, leading to thicker adsorbed polycation layers with more loops. This, in turn, promotes the adsorption of thicker anionic PCBS layers. Similar results were found for ISAM films made of PCBS and PDDA (FIG. 3c). Table 1 (FIG. 3d) shows that, for both polycations, the bilayer thickness increased substantially as the pH of the polycation solutions increased from 7 to 11 while the pH of the PCBS solution was held fixed at 7. The bilayer thickness for PCBS/PAH films increased by a factor of ~50× as the pH of the PAH solution increased from 7 to 11, while there was a ~70× increase in the bilayer thickness for PCBS/PDDA films. The data in FIG. 3d and in FIGS. 2a and 2b and demonstrate that the film thickness and refractive index can both be readily controlled. For completeness, the deposition conditions were: no added salt, polycation concentration 10 mM, PCBS deposition done at pH 7.0 and 10 mM. Reported error values represent the standard deviations.

Figure 3E:
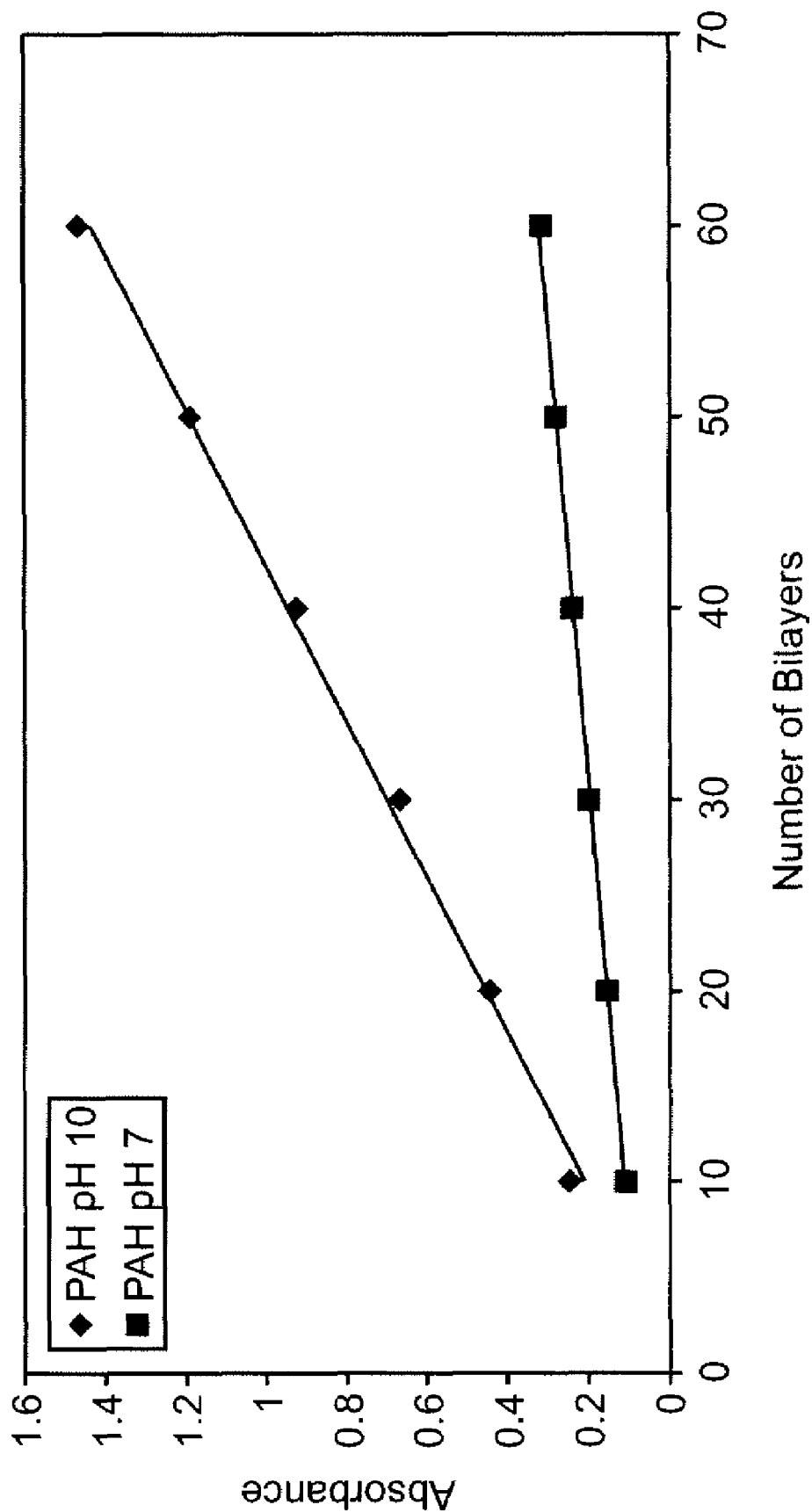

The PCBS composition of the ISAM films and, hence, the refractive index of the films, decreases as the fraction of polycation adsorbed in loop-like conformations increases. A characteristic of ISAM deposition is the linear increase of the absorbance of the film with the number of bilayers deposited. Since the polycations are transparent at 359 nm, the slope of this linear relationship between absorbance and bilayer number reflects the amount of PCBS deposited per bilayer. A typical plot of the absorbance vs. the number of bilayers for PCBS/PAH films is shown in FIG. 3e. The absorbance/bilayer slope for PCBS/PAH films increased by a factor of 10 as the pH was changed from 7 to 11 while a ~3× increase was seen with films made with PDDA. However, the PCBS fractional content of the film, as shown by the absorbance/nm values (the ratio of the absorbance/bilayer and the bilayer thickness values) in Table 1, decreased by ~5× for PAH and by 20× for PDDA when the polycation deposition pH varied from 7 to 11. These large decreases in the PCBS content directly control the refractive indices of the films.

Returning to FIGS. 2a and 2b, thickness and Refractive Index of PCBS/PAH ISAM films consisting of 20 bilayers is shown as a function of pH of the dipping solutions. These graphs demonstrate that precise control of the refractive index of ISAM films can be achieved to the level needed for tuning LPG sensitivity. The refractive index of PCBS/PAH films can be tuned over the range 1.67-1.75 by varying the pH of the PCBS and PAH dipping solutions while the total film thickness (20 bilayers) can be varied from ~5-75 nm. When combining high n PCBS with low n PAH, increasing the pH of the PAH solution from 7 to 10 (above the pKa) leads to an increased PAH layer thickness that increases the fraction of PAH (low n) in a bilayer and thus decreases the refractive index of the composite film. Other polyanion/polycation combinations are possible as well to provide a much wider tunability of the refractive index of ISAM films. Use of two non-conjugated polyelectrolytes results in refractive index values in the range 1.5-1.6.

In regard to fiber design of LPGs, characteristics such as compactness, low insertion loss, low back reflection, and high resolution make long-period gratings attractive as gain flattening filters, spectral shapers, and mode converters in optical fiber communication systems as alluded to above. LPGs couple light from the fundamental mode to higher order guided or cladding modes (HOM) in a fiber. If the HOM is lossy in nature, as is the case with cladding guided modes, sharp absorption lines are obtained in the fiber's transmission spectrum. The cladding modes are, through the evanescent field, sensitive to the index of the medium surrounding the fiber so that changes in external refractive index will shift the wavelength of the absorption lines. This sensitivity to ambient index has led to extensive investigations of fiber LPGs as chemical and biological sensors. However, the realization of efficient index-sensing devices with LPGs critically depends on the ability to precisely control the optical properties (refractive index, loss) of the material surrounding the LPG-based fiber device. Specifically, the effective refractive index of the ambient medium must be as close as possible to (but lower than) the refractive index of the glass cladding of a fiber, to achieve LPGs that are ultra sensitive to ambient refractive index changes. This regime has previously been studied, although not in minute detail since accurate control of the ambient refractive index to within $10^{-5}$ of that of the cladding, is hard to achieve. One key innovation is using the ISAM process to provide an exceptional level of control over the refractive index and thickness of the material surrounding an LPG. The inventors have shown that LPGs can be highly sensitive to nm thick films in the cladding exterior, as opposed to the refractive index of a bulk exterior medium. ISAM films should prove to be the coating of choice for realization of LPG device functionalities that require extreme index sensitivities.

According to the LPG resonant condition equation, $$\lambda_{res} = (n_{core} - n_{clad})\lambda \quad (1)$$

where $\lambda_{res}$ is the resonant wavelength, $n_{core}$ is the effective index of the fundamental core mode, $n_{clad}$ is the effective index of the coupled cladding mode, and $\lambda$ is the grating period. Therefore, $\lambda_{res}$ of the LPG is determined by both n and $d_{tot}$ of the ambient coating because $n_{clad}$ is a function of both and their effect on $n_{core}$ is negligibly small for SMF.

Since it is the effective index of the coupled cladding mode that is significant, it is possible to observe shifts of $\lambda_{res}$ when thin films with index larger than that of the cladding are deposited on the cladding exterior. This is in contrast to the case in which the fiber is immersed in a bulk medium of higher index. In the latter case, there is diminished coupling which cannot be spectrally tuned. This is because the higher ambient index medium frustrates total internal reflection (TIR) at the glass-cladding surface, a condition necessary for the existence of well-guided cladding modes. In such cases, a substantially weak resonance is obtained. Moreover, changes in the index of the ambient would not cause spectral shifts. This is because a leaky mode is not guided due to TIR, but exists because of (weak) Fresnel reflections at the glass-ISAM boundary, and such reflections have no spectral phase dependence. The data of FIG. 3a show, for example, that $\lambda_{res}$ shifts due to changes in index as well as thickness of the ISAM films. The changes in ISAM deposition conditions (leading to changes in their indices) clearly produce spectral shifts of strong resonances for index values larger than that of the cladding as shown in FIG. 3b. This may be understood by considering the mechanism of coupling in ISAM coated LPGs.

The fact of the coupled cladding mode existence may be qualitatively understood from the following: In the case of that the LPG is coated with approximately infinite-thick ambient medium the refractive index of which is higher than that of the fiber cladding, the coupled cladding mode will be cut off. At this point, the fundamental core mode will be coupled into the leaky mode, which induces energy loss into the ambient medium. In comparison, in the case that the LPG is coated with only nm-thick ambient medium and the outermost medium is air, as shown in FIG. 2, although the refractive index of the ambient medium is higher than that of the fiber cladding, the mode field will be overlapped with the air substantially. Therefore, the average ambient index determined by the refractive indices of both the ambient medium and the air will be smaller than that of the fiber cladding. As a result, the coupled cladding mode still exists without cutoff.

The evanescent tail of the cladding-mode field normally extends by 100-200 nm into the ambient medium. Since all the ISAM films investigated are thinner than this value, the cladding mode interrogates both the ISAM as well as the surrounding air. The effective index $n_{eff}$ of a guided mode can be approximated by:

$$n_{eff}^2 \sim \int \int n^2(r) \cdot |E(r)|^2 \cdot dA \quad (2)$$

where $E(r)$ is the mode field distribution, $n(r)$ is the refractive index profile of the fiber, and $\int\int dA$ signifies an integration across the cross-sectional area of the fiber. Equation 2 shows that the effective index of a mode is approximately proportional to the average refractive index of the region in which light exists, weighted by the local intensity profile. Since a typical cladding mode samples both the high index ISAM as well as the surrounding (low index) air, the average index of an ambient comprising 10-50-nm thick ISAM films and air is that of an equivalent bulk medium with index lower than silica. Moreover, this average index value will depend on the film-thickness in addition to the index of the film, with thicker films leading to a larger ISAM contribution to the average index, as is evident from Eq. 2.

In summary, deposition of nm-thick ISAM films on LPGs for the first time has been demonstrated to yield properties useful both as LPG tuning mechanisms as well as platforms for sensing devices. Fine control of the refractive index and the thickness of the ISAM film was achieved by altering the relative fraction of the anionic and cationic materials deposited layer-by-layer. This highly controllable deposition-technique facilitates fine-tuning grating properties. ISAM films with sub-wavelength thicknesses cause dramatic resonant wavelength shifts of LPGs, which enables their use as sensors of target compounds. Additional experimental data showing the efficacy of the present invention to provide tuning of LPGs is provided in the above-incorporated U.S. Provisional Patent Application.

Chemical Sensor and Bio-Sensor Applications

Biological sensors have the potential to revolutionize the way genomics, proteomics, diagnostics, and environmental monitoring are performed. Genomics and proteomics require high-throughput, sensitive assays for the detection of intermolecular interactions. The identification and characterization of large numbers of protein-protein contacts is a central theme in the growing field of Systems Biology. Furthermore, rapid, specific, and sensitive detection of organisms and their products is essential for early identification of pathogens and other organisms in an environment, whether it be in a host body, in a public venue, in an industrial setting, or in a natural ecosystem. This can apply to well-known pathogens, to emerging infectious agents, to biowarfare agents, and to environmental contaminants, where rapid and early detection is critical. Simple conventional colorimetric assays yield rapid results, but they lack the sensitivity needed for detection of microbes and toxins that may be present in environmental samples. Highly sensitive immunoassays, cellular response assays, and "lab on a chip" formats have been developed, but they generally require multiple or specialized reagents, and some formats can be time-consuming.

In general, biosensor platforms use specific biomolecular recognition between an affinity ligand or enzyme and the target biomolecule (protein, toxin, cell, etc.). The ligand/target binding event is transduced into a measurable signal by a variety of methods: e.g., enzymatic reaction, refractive index change at the sensor surface, change in electrical or acoustic properties, or incorporation of fluorescently or radioactively labeled reagents. In all biosensor applications, the most important features are specificity, sensitivity, and the time required to attain a positive or negative signal. Furthermore, if a sensor platform is to be used in the field, it must be portable, simple to operate, and rugged. Ideally, the ligand/target binding event should be transduced to a measurable signal without requiring the use of complex protocols or fluorescently- or radioactively-labeled reagents. A biosensor platform that combines the features of sensitivity, specificity, portability, and simplicity is needed to respond to the many challenges in life sciences research, environmental monitoring, and national security.

The invention, as applied to chemical sensors and biosensors such as those described above integrates recent developments in nanoscale self-assembled films, fabrication of novel optical fiber long-period gratings (LPG), and molecular biology to enable a radically different, highly sensitive platform for the detection and analysis of biological species. The sensor platform in its simplest and preferred form comprises a self-assembled multilayer affinity coating on an LPG. As described above, the existence of an LPG in the optical fiber causes a strong decrease in the transmitted light intensity at a specific wavelength, referred to as the attenuation wavelength. Since the attenuation wavelength can shift as a function of the environment exterior to the optical fiber cladding, LPGs have been considered for sensing applications. While LPGs have been shown to exhibit sensitivity to the refractive index of the bulk external medium, this level of sensitivity is not suitable for detection of biomolecules because: 1) the biomolecules are often present at very low concentrations in the environment and thus affect the bulk index negligibly and 2) there is no specificity since the presence of any species at moderate concentration will alter the refractive index. Thus, to detect biomolecules using an LPG, two steps are needed: 1) a coating with controlled thickness and refractive index must be deposited onto the LPG cladding in order to tune the LPG to maximum sensitivity and 2) an affinity film must then be installed on top of the "tuning" film that will selectively bind to a target biomolecule to produce a shift in the attenuation wavelength. This second film provides the necessary specificity of detection while the first film provides the necessary sensitivity.

Until now, no practical approach has been demonstrated for making an LPG with the necessary sensitivity and specificity to function as an effective biosensor. However, through careful design of the LPG parameters and self-assembled film optical properties, the inventors have recently shown that shifts in the attenuation wavelength in response to adsorption of a layer only 1 nm thick can be easily observed, as described above. Furthermore, the polyelectrolytes used to form the self-assembled film are easily deposited under ambient conditions in a matter of minutes and possess amine or carboxyl groups, which provide facile binding sites for incorporation of a wide range of affinity ligands to enable detection of a vast array of target species. Further, the inventors have experimentally demonstrated this using the model biotin-streptavidin system.

The biosensing platform of the invention is analogous to those based on surface plasmon resonance (SPR), such as the BiaCore system, but has significant advantages while systems using SPR lack a number of the above-enumerated properties and are thus impractical for many desired applications. In SPR, light is reflected off the interface of a substrate (e.g. glass without any grating structure) and a thin conducting film (e.g. gold). At a particular angle of incidence, the reflection is strongly reduced due to coupling with the surface plasmon mode in the gold film. This angle is altered by the refractive index of the material on the opposite side of the gold film. The basic mechanism of operation of SPR, then, is to attach an affinity ligand to the gold surface. This is typically done by formation of a thiol-on-gold self-assembled monolayer, which takes hours to form. The affinity ligand is then attached to the thiol. When the target species is present, it binds to the ligand causing a change in the local refractive index. The altered refractive index is then observed through the change in the angle at which minimum reflection occurs. The angle typically must be measured to an accuracy of <0.001°, which makes SPR sensors expensive, delicate, and non-portable. However, because the same platform can be employed to detect a vast array of species simply by altering the affinity ligand, SPR sensors have established a critical role in a wide range of biological applications including fundamental analysis of protein-protein interactions, high-throughput screening for drug discovery, and detection of food contamination.

The LPG sensor platform of the invention also operates by detection of changes in local refractive index at an interface. However, in sharp contrast thereto, the refractive index change is monitored through a change in the attenuation wavelength transmitted through the fiber rather than incident angle reflection. The approach in accordance with the invention is thus far less sensitive to optical alignment issues, making it more rugged and portable. Furthermore, it is possible to fabricate LPGs that respond to the index change with a broadband change in the transmitted intensity, rather than a wavelength shift. With such turn-around-point (TAP) LPGs (see below), detection can be made with a simple power meter, rather than a spectrum analyzer, yielding a very inexpensive sensor platform. Importantly, the sensor platform can be utilized for detection of any biological species, from molecules to whole cells, so long as an appropriate affinity ligand is available. A key feature of the sensor platform in accordance with the invention is the use of a versatile self-assembly mechanism based on electrostatic attraction that easily deposits nanometer thick films on the surface of a silica optical fiber in a matter of minutes. In fact, thiol-on-gold self-assembly is not even applicable to LPG sensing of the invention due to the screening of the optical field to the fiber exterior by the gold layer.

The overall objective of the invention in regard to chemical sensors and biosensors is to provide a new biosensor platform based on nanometer-thick self-assembled layers on long-period gratings (LPGs) that has the potential for exceptional sensitivity, low cost, field portability (ease of use), and rapid detection of target species. As described above, an LPG is a periodic modification of the refractive index in the core of an optical fiber that can be exquisitely sensitive to the environment surrounding the fiber cladding. Adsorption of a species to the cladding alters the effective refractive index, and thus generates a signal. Thus, if a target molecule binds to an affinity ligand on the cladding, a signal is generated in seconds, without the need for additional reagents.

Figure 4:
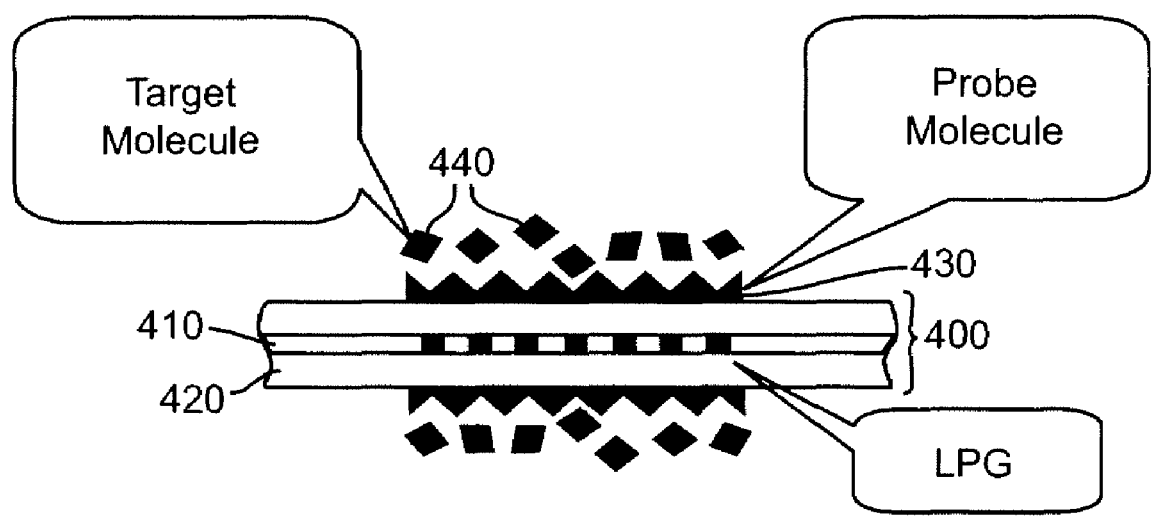
FIG. 4 is a schematic diagram of an optical fiber LPG biosensor with an ISAM affinity ligand in which binding leads to a measurable change in refractive index that affects the intensity of transmitted light in the optical fiber.

FIG. 4 is a schematic diagram of an optical fiber LPG biosensor with an ISAM affinity ligand. It will be recognized that the structure 400 illustrated in FIG. 4 is similar to that produced by the process illustrated in FIG. 1 but with the cladding 420 surrounding a fiber optic LPG (as contrasted with a generic substrate in FIG. 1) and with the ISAM film 430 being preferably very thin (to maximize the change in overall refractive index of the film when target molecules 440 are bound thereto) and terminating with a layer of probe molecules 430 having an affinity for binding to specific target molecules 440. Binding of a target molecule thus leads to a measurable change in refractive index that affects the intensity of transmitted light in the optical fiber.

The transmission spectrum of a conventional LPG has a sharp attenuation peak in the intensity of the transmitted light that is due to coupling between core and cladding modes of the fiber at resonant wavelengths. This resonant condition can be quite sensitive to the refractive index of the ambient medium outside the cladding.

Figure 5:
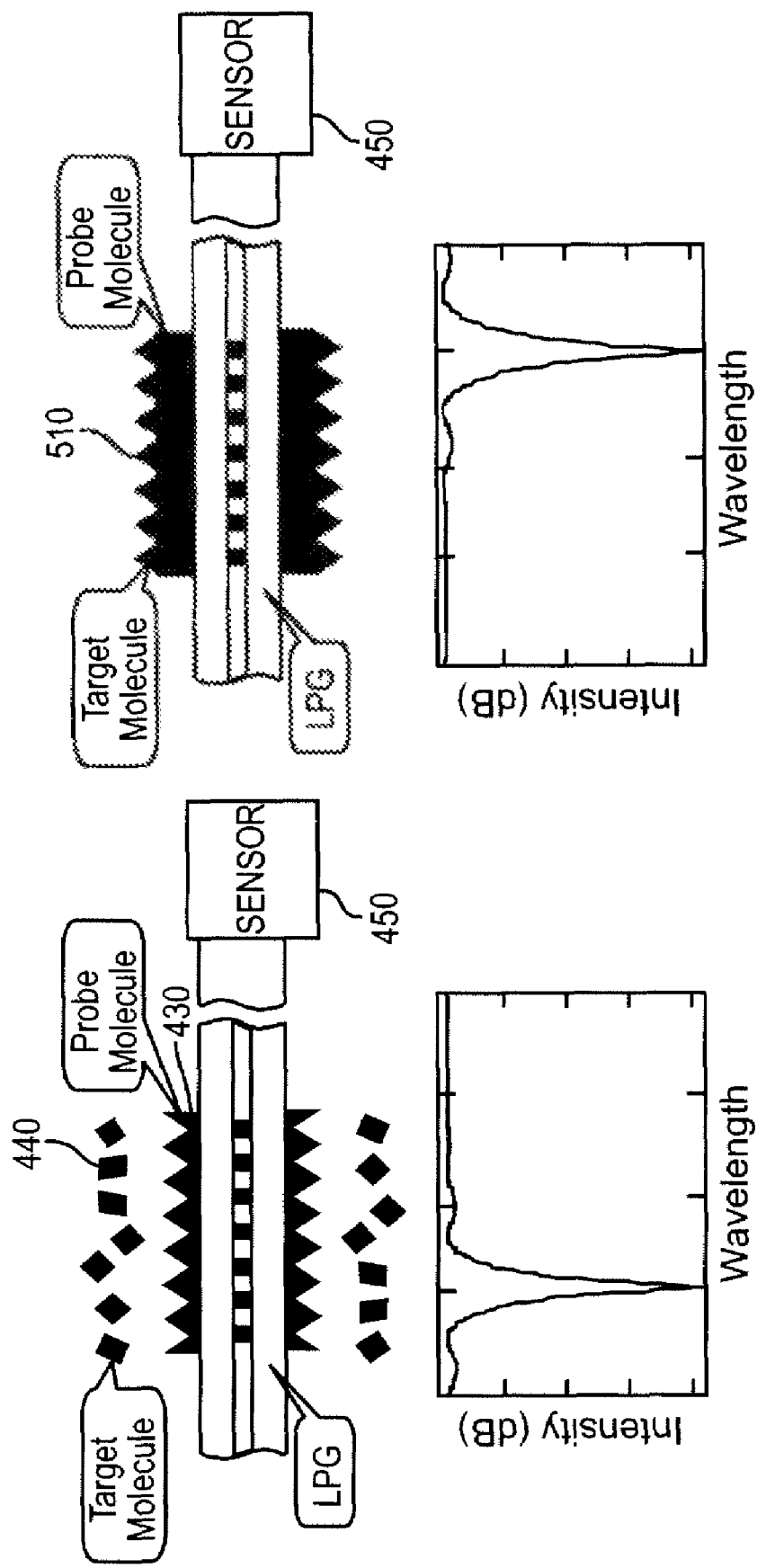
FIG. 5 illustrates the effects of binding of target molecules on the LPG chemical sensor or bio-sensor of FIG. 4, FIGS. 6a, 6b and 6c illustrate broadband mode coupling and true amplitude (intensity) modulation with ambient refractive index changes in fibers designed to have identical group velocities of the fundamental mode and high order guided or cladding mode (HOM) in a given spectral range.

The inventors have recently found that remarkably large shifts in the attenuation wavelength can be produced by the adsorption of a single polyelectrolyte monolayer on the fiber cladding as illustrated in FIG. 5. The binding of target molecules, as illustrated, changes both the thickness of the film and the average refractive index to a greater or lesser degree; the combination of which has been found to provide a strong shift in attenuation wavelength which is readily detectable. This exceptional sensitivity to ultra-thin coatings enables the development of a highly promising biosensor platform as illustrated in FIG. 4. An ionic self-assembled multilayer (ISAM) film is deposited, as described in connection with FIG. 1, on the cladding of an LPG in a manner that optimizes the sensitivity and is subsequently functionalized with an affinity ligand. The LPG is then exposed to a liquid or gaseous environment that potentially contains the target species. If the target species is present, it will specifically bind to the immobilized ligand, resulting in an increased thickness and a change of the effective refractive index of the coating 510; shifting the maximally attenuated wavelength, as illustrated in FIG. 5 which can be detected at sensor 450.

Figure 6A:
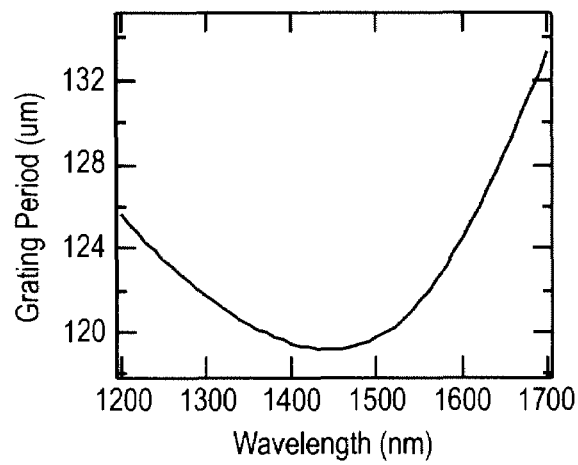
FIG. 6d illustrates TAP-LPG transmission spectra of bare LPG and after deposition of 1.5 bilayers of PAH/PCBS, biotin and streptavidin at concentrations of 12.5 to 100 µg/mL (top to bottom)
Figure 6B:
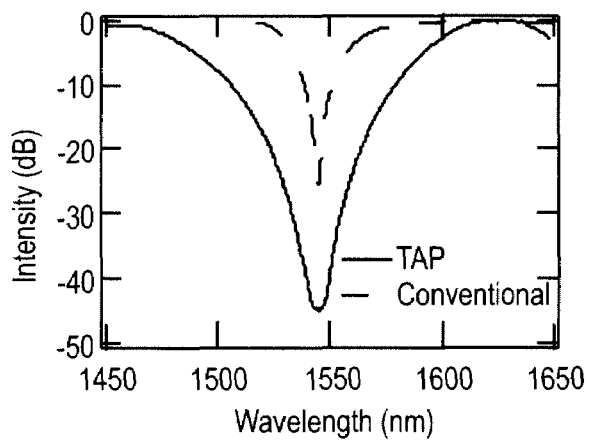
Figure 6C:
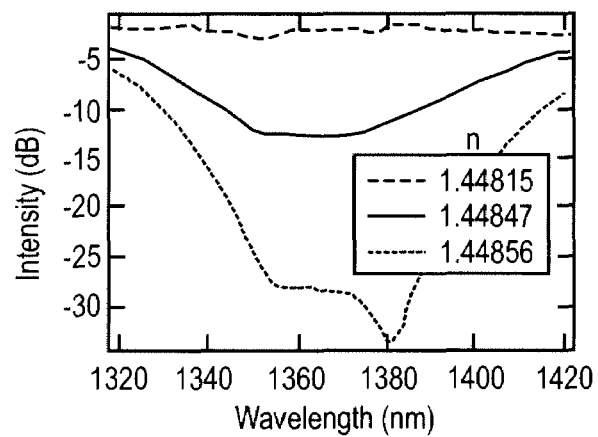

The spectral response of an LPG to ambient index changes can be radically altered by designing fibers with special dispersive properties. For instance, fibers in which the fundamental mode and a HOM are designed to have identical group velocities in a given spectral range, result in extremely broadband mode coupling, and true amplitude (intensity) modulation with ambient refractive index changes, as illustrated in FIGS. 6a-6c. The phase matching curve (PMC) of LPGs in dispersion engineered fibers possess a turn-around-point (TAP), where its gradient is zero, as shown in FIG. 6a. This is in contrast to the monotonically varying PMCs in conventional fibers, and results in bandwidths exceeding 40 nm for 99% mode-conversion from the fundamental mode to the HOM (see spectrum on FIG. 6b). Tuning such LPGs, by varying the ambient index, results in true intensity modulation, rather than a spectral shift of the resonance, as shown in FIG. 6c. The experimental data from OFS laboratories show that at 1380 nm, for example, the attenuation offered by the LPG for nsur=1.44856 is 99.9% (−30 dB=decrease of $10^{-3}$) of the intensity measured for nsur=1.44815, corresponding to a bulk refractive index change of $4 \times 10^{-4}$. Since intensity changes of 10% or less can be easily measured, exceedingly small refractive index changes on the order of $10^{-6}$ can be resolved using TAP-LPGs. And, in principle, TAP-LPGs can be designed with arbitrarily high refractive index sensitivity. This enables a highly cost effective sensing device, because intensity measurements are significantly easier to implement than spectrally sensitive measurements.

As an alternative to sensing the maximally attenuated wavelength, novel turn-around-point (TAP) LPGs have been developed that have yielded the highest sensitivity to ambient refractive index yet observed (25 dB modulation in the strength of the LPG resonance for an ambient index change $\Delta n$ of only $2.7 \times 10^{-4}$). To form TAP LPGs, after the fiber is fabricated and an LPG at the appropriate grating period written, the TAP condition can be induced by slightly etching the silica cladding of the fiber to shift the phase matching condition (PMC) in the appropriate direction. The PMC can also be shifted by coating the LPG with ISAM films. Since ISAM coating and cladding serve to shift the PMC in opposite directions, the position of the PMC can be arbitrarily controlled. Thus, application of these two steps recursively will ensure that the TAP condition can be met for any composition of ISAM films and even for a composite structure that comprises an ambient of water for the ISAM coated LPGs. In addition, the ability to dispersion engineer the fiber itself will ensure that any desired resonance bandwidth can be obtained for any combination of ISAM films and ambient environment The desired final outcome of these recursive steps of fiber design, determination of the optimal number of ISAM bilayers, and etching of cladding, would be to obtain a broadband TAP resonance of the type shown in FIG. 6b for any ISAM coated LPG immersed in water.

Importantly, TAP gratings undergo a broadband change in transmittance rather than a wavelength shift and thus have the additional major advantage that sensing can be achieved with an inexpensive power meter rather than a spectrum analyzer. LPG biosensors operating in the vicinity of the turn-around-point are expected to be dramatically more sensitive than conventional LPGs. That is, changes in the effective refractive index of the ISAM coating on the order of $10^{-6}$ may be observed simply by monitoring the transmitted power through the device. This sensitivity is higher than that observed in the latest SPR devices (e.g., BiaCore 3000). However, unlike SPR, a fiber optic-based sensor platform does not require precision alignment of optical components and will be highly portable. Thus, it is expected that the TAP-LPG sensor platform will enable attaining of the objectives of sensitivity, specificity, and simplicity, as well as inexpensive and highly portable equipment. It is also important to note, in this regard, that the ISAM films are easily and economically removable, using appropriate acids, and replaceable; providing the ability of repeating the process to provide a renewed sensor for the same or a different target molecule using the same LPG. Further, this capability ensures that the LPG will not be rendered useless in the event of errors in the ISAM film formation process.

Figure 6D:
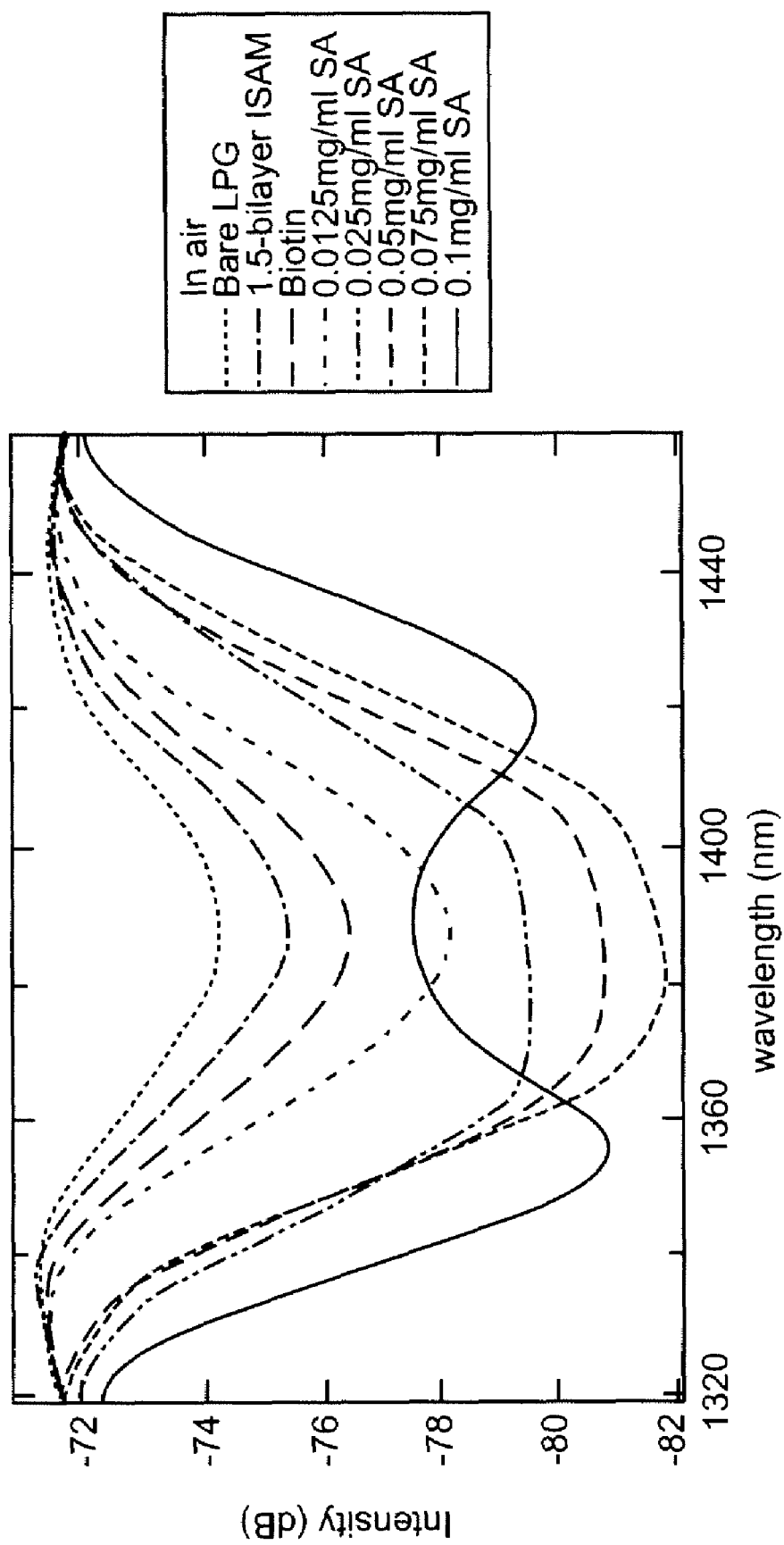
Figure 7:
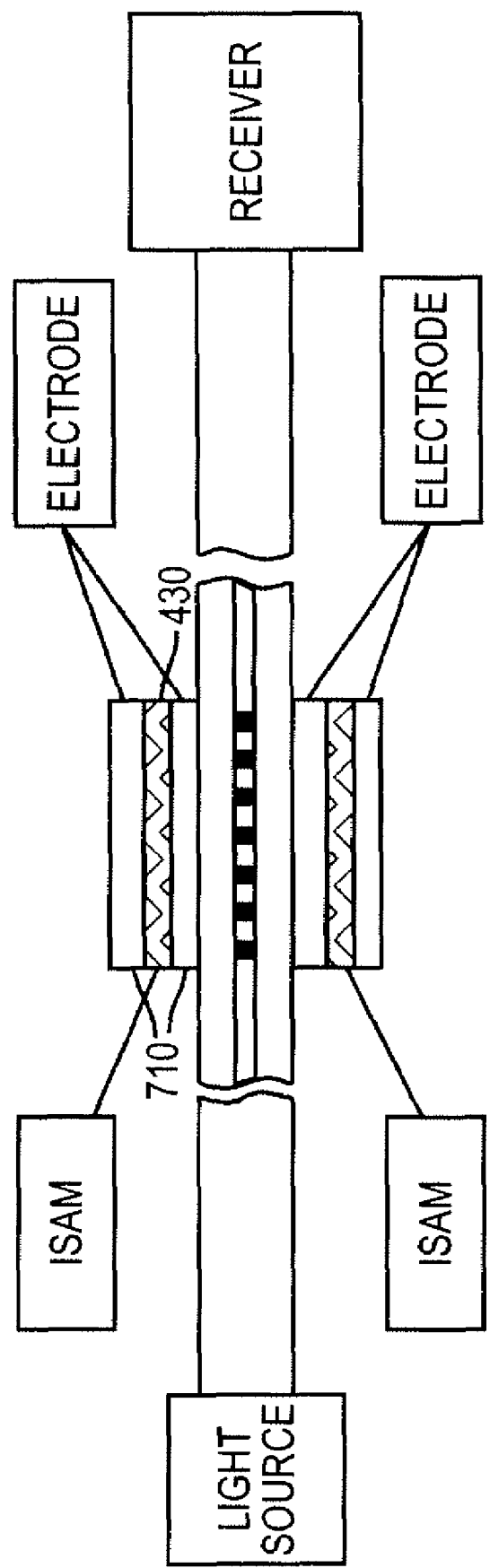
FIG. 7 is a cross-sectional view of an embodiment of the invention configured as a modulator within a fiber-optic communication system.

To establish proof-of-concept, the inventors have used the very strong affinity ($K_d=10^{-15}$M) biotin-streptavidin interaction as an initial model system. This was done on a grating etched to the TAP point for an ambient of air. Starting with ISAM films of PCBS-PAH on a TAP LPG with PAH as the terminal layer, the primary amines of the PAH sidegroups were biotinylated using the biotin-N-hydroxysuccinimide ester (biotin-NHS). FIG. 6d shows preliminary data in which 1.5 bilayers of PAH/PCBS were first deposited on the bare fiber to provide amine groups on the exterior. The fiber was then exposed to biotin and then to streptavidin at concentrations of 12.5 to 100 µg/mL. While the measurements in this initial study were made in air, they can be made equally well in solution to yield kinetic data by etching the fiber so that the TAP condition occurs for the refractive index value of the liquid. The 2 dB change in transmitted intensity at 1390 nm for the biotin versus the 12.5 µg/mL streptavidin corresponds to a 37% change in intensity.

In the interest of completeness of this description of the invention and its preferred embodiments, the critical variables that lead to maximum sensitivity of an LPG upon the adsorption of a nm-thick self-assembled film will now be discussed. This will be done in two steps:

(a) Self-assembled films on conventional LPGs—experimental results thus far indicate that the refractive index of the adsorbed layer is one of the most critical quantities and that it should be significantly larger than that of the cladding. This is in marked contrast to the sensitivity of LPGs to ambient refractive index where sensitivity increases as the ambient index approaches the cladding index. In addition, the sensitivity of conventional LPGs is also governed by the difference in group velocities between the core and the cladding mode. Fibers are thus preferably designed to optimize this group velocity difference to yield highly sensitive LPGs coated with nm-thick self-assembled films.

(b) Self-assembled films on TAP LPGs—These optical fibers have the potential for much higher sensitivity for biosensors than do the conventional LPGs while being more economical. Since TAP LPGs involve coupling the fundamental mode to a very high order cladding mode, more of the evanescent field of the cladding mode interrogates the self-assembled film, leading to dramatically different effective refractive indices for the self-assembled layers. The optimal thickness of the films will be determined for specific higher order cladding modes that yield TAP LPGs, so as to exploit the enhanced sensitivity of TAP LPGs. Ligand functionalization procedures developed earlier will not need to be modified for TAP gratings, but the evaluation and measurement procedures are preferably modified (indeed simplified) for sensors employing self-assembled films with TAP LPGs.

Additionally, it is preferable to attach affinity ligands to ISAM films adsorbed onto the LPG cladding so that the sensitivity to target species is maximized and the sensor operation is robust. Ligand-target combinations preferably use biotin-streptavidin as a model system to optimize immobilization and analysis conditions, although other systems with specific research or practical applications can be used. Several different classes of affinity ligands, including peptides, enzymes, aptamers and antibodies may affect the flexibility of the LPG sensor. For example, systems may include the flavonoid multienzyme complex, to test the utility of the sensor for defining protein interaction interfaces in vitro, and *B. anthracis*, as a model for detecting infectious disease agents in biological fluids.

Optical Modulator for Fiber-Optic Communication Systems

Referring now to FIG. 7, there is shown in cross-section, a variant form of LPG/ISAM structure usable as an optical modulator. In this variant of the invention, the LPG 410 and cladding 420 are provided as before and any of the above-discussed techniques of tuning the LPG may be employed, including the use of a TAP LPG. However, for use as an optical modulator, the ISAM film material is chosen to have an electro-optic response either by change of dimensions (e.g. through application of electrostatic force or piezo-electric or magnetostrictive effects or the like) or by change of refractive index in response to an electrical field; suitable materials for which are known. An example of an ISAM film having the latter property is described in U.S. Pat. No. 6,953,607 which is hereby incorporated by reference in its entirety. By sandwiching the ISAM film between electrodes (the electrode adjacent the LPG being transparent) in a concentric manner around an LPG, application of a voltage between the electrodes will cause a change of intensity of transmitted light at a specific wavelength or a range of wavelengths in the case of a TAP LPG. As with the sensors described in detail above, such an arrangement would then serve as an optical modulator for use in a fiber-optic communication system or other application requiring modulation of light. Since the effects causing shift can be achieved very rapidly by either or both of the above effects changing the thickness and/or refractive index of the ISAM film, such an optical modulator can exhibit a wide bandwidth.

In view of the foregoing, it is seen that, until recently, optical fiber long-period gratings were only recognized as being sensitive to the refractive index of the ambient environment, defined by a bulk refractive index value. The inventors have found that LPGs can be remarkably sensitive to the presence of self-assembled layers of nanometer-scale thickness. While it is clear that this effect is due to the modification of the propagation constants of the cladding modes, the detailed identification of the critical factors yielding this high sensitivity allows a simple and economical technique of tuning LPGs, providing a robust, portable economical and reusable chemical sensor or biosensor and/or a simple and inexpensive tunable optical modulator. The recent development of turn-around-point LPGs enables an unprecedented level of sensitivity in LPGs in combination with the principles of the present invention. Utilization of ionic self-assembled multilayers on LPGs allows simple, rapid deposition of nm-thick layers with surface groups (e.g. amine, carboxy) amenable to attachment of a wide variety of important ligands. Together, these advances provide a unique opportunity for development of a powerful, new biosensor platform that does not require labeled reagents for detection.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. An optical device comprising, in combination, a fiber-optic element including a turn-around-point long period grating (TAP LPG) therein, a multi-layer film adjacent said TAP LPG included in said fiber-optic element having a higher index of refraction than said fiber-optic element, and an ambient environment.

2. An optical element as recited in claim 1, wherein said fiber-optic element includes cladding and said multi-layer film has a higher index of refraction than said cladding.

3. An optical element as recited in claim 2, wherein said cladding has a lower index of refraction than a core of said fiber-optic element.

4. An optical element as recited in claim 1 wherein said multi-layer film is an ionic self-assembled multi-layer (ISAM) film.

5. An optical element as recited in claim 4 wherein said ISAM film includes at least one of synthetic polyelectrolytes, proteins, fullerenes, metal colloids, clays and multivalent dye molecules.

6. An optical element as recited in claim 1 wherein said multilayer film includes respective layers of PAH and PCBS.

7. An optical element as recited in claim 1 wherein said multi-layer film includes a layer of biotinylated PAH.

8. An optical element as recited in claim 1 wherein said multilayer film includes a layer of probe or receptor molecules.

9. An optical element as recited in claim 8 wherein said probe or receptor molecules include a receptor ligand.

10. An optical element as recited in claim 1 wherein said multi-layer film includes a material exhibiting a change of dimension or refractive index in response to an electric field, said optical element further including an electrode adjacent said multi-layer film.

11. An optical element as recited in claim 1 wherein said TAP LPG includes said multi-layer film.

12. an optical element as recited in claim 11, wherein said multi-layer film shifts a phase matching curve (PMC) position to meet turn-around-point conditions of said TAP LPG.

13. A chemical sensing or biosensor apparatus comprising a fiber-optic element including a long period grating therein, a multi-layer film adjacent said fiber-optic element having a higher index of refraction than said optical fiber element, said multilayer film including a layer of probe or receptor molecules, and means for detecting changes of light attenuation in said fiber-optic element.

14. An apparatus as recited in claim 13 wherein said means for detecting changes of light attenuation includes a spectrum analyzer.

15. An apparatus as recited in claim 13 wherein said fiber-optic element includes a TAP LPG and wherein said means for detecting changes of light attenuation comprises means for measuring broadband light intensity.

16. An apparatus as recited in claim 13 wherein said layer of probe or receptor molecules include an affinity ligand.

17. A fiber optic communication system comprising a fiber-optic element including a long period grating therein, a multi-layer film adjacent said fiber-optic element having a higher index of refraction than said optical fiber element, said multi-layer film including a layer of material exhibiting an electro-optical response to an electric field, and an electrode for applying an electrical field to said multi-layer film.

* * * * *